（12）United States Patent
Hernandez

(10) Patent No.: US 7,143,900 B2
(45) Date of Patent: Dec. 5, 2006

(54) SEPARATION DEVICE AND METHOD OF MAKING THE SAME

(75) Inventor: Juan J. Hernandez, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 67 days.

(21) Appl. No.: 10/282,345

(22) Filed: Oct. 28, 2002

(65) Prior Publication Data
US 2004/0079696 A1 Apr. 29, 2004

(51) Int. Cl.
B01D 63/00 (2006.01)
B01D 29/00 (2006.01)
B01L 11/00 (2006.01)

(52) U.S. Cl. .......... 210/498; 210/321.75; 210/321.84; 210/456; 422/101; 422/104

(58) Field of Classification Search .......... 210/321.84, 210/456, 498, 500.25, 500.26, 321.6, 321.75; 422/101, 104; 216/2, 87, 94, 97, 99, 100; 200/243, 769
See application file for complete search history.

(56) References Cited

U.S. PATENT DOCUMENTS

| | | | |
|---|---|---|---|
| 4,797,211 A * | 1/1989 | Ehrfeld et al. .......... 210/321.84 |
| 5,304,487 A * | 4/1994 | Wilding et al. ................ 435/29 |
| 5,543,046 A | 8/1996 | Van Rijn | |
| 5,792,354 A | 8/1998 | Aksberg | |
| 5,807,406 A | 9/1998 | Brauker et al. | |
| 6,044,981 A | 4/2000 | Chu et al. | |
| 6,368,871 B1 * | 4/2002 | Christel et al. ............. 436/180 |
| 6,440,725 B1 * | 8/2002 | Pourahmadi et al. .... 435/288.5 |

* cited by examiner

Primary Examiner—Krishnan S. Menon

(57) ABSTRACT

A separation device, such as a filter or separation line apparatus, and method of making the same.

11 Claims, 7 Drawing Sheets

SEPARATION DEVICE AND METHOD OF MAKING THE SAME

BACKGROUND OF THE INVENTIONS

Separation devices come in many forms and are used in many ways. Mechanical separation devices, which are sometimes referred to as "filters," are commonly used to remove particles from fluids. Separation lines, on the other hand, are typically in the form of long, expensive tubes that are used to separate compounds into their individual components. When a fluid compound is driven through a separation line, the compound will separate into its individual components prior to reaching the end of the line due to differences in the molecular weights of the components. One common use of separation lines is spectroscopy, such as gas chromatography mass spectroscopy ("GCMS"), Fourier transform infrared spectroscopy ("FTIR") and ultraviolet/visible spectroscopy ("UV VIS").

The inventor herein has determined that conventional separation devices are susceptible to improvement. For example, the inventor herein has determined that it would be desirable to provide mechanical separation devices that are well suited for the removal of small particles from small fluid volumes and are also relatively inexpensive to manufacture. The inventor herein has also determined that it would be desirable to provide separation line apparatus that pack long separation lines into relatively small volumes and are also relatively inexpensive to manufacture.

BRIEF DESCRIPTION OF THE DRAWINGS

Detailed description of preferred embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

Figure 1:
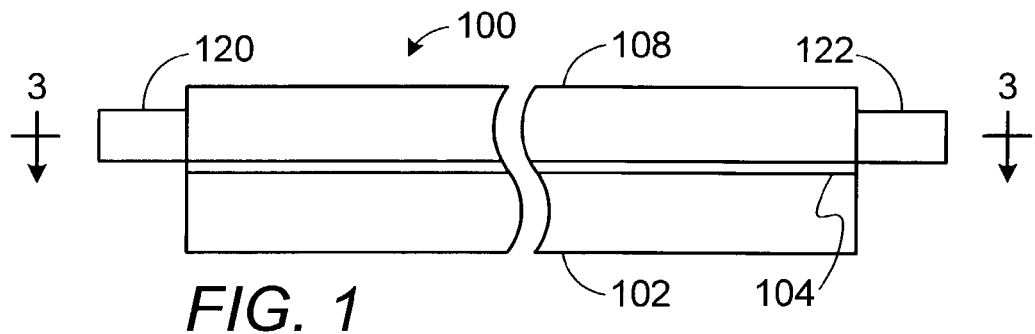
FIG. 1 is a side view of a separation device in accordance with a preferred embodiment of a present invention.
Figure 2:
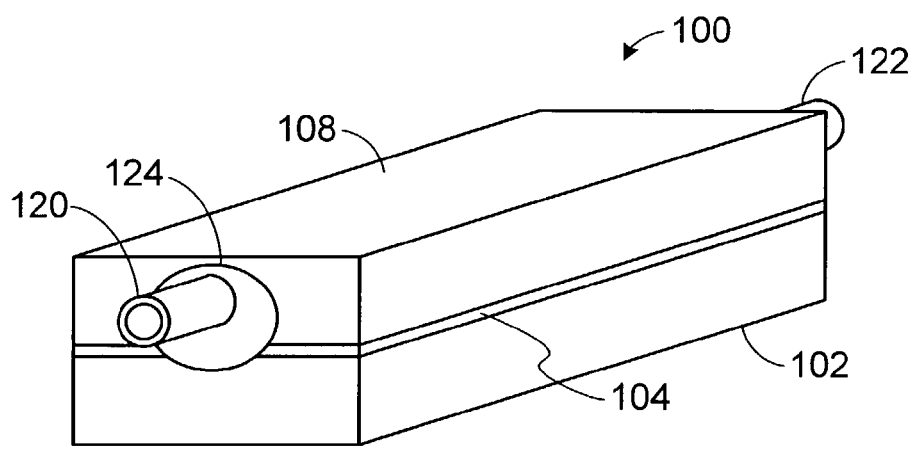
FIG. 2 is a perspective view of the separation device illustrated in FIG. 1.
Figure 3:
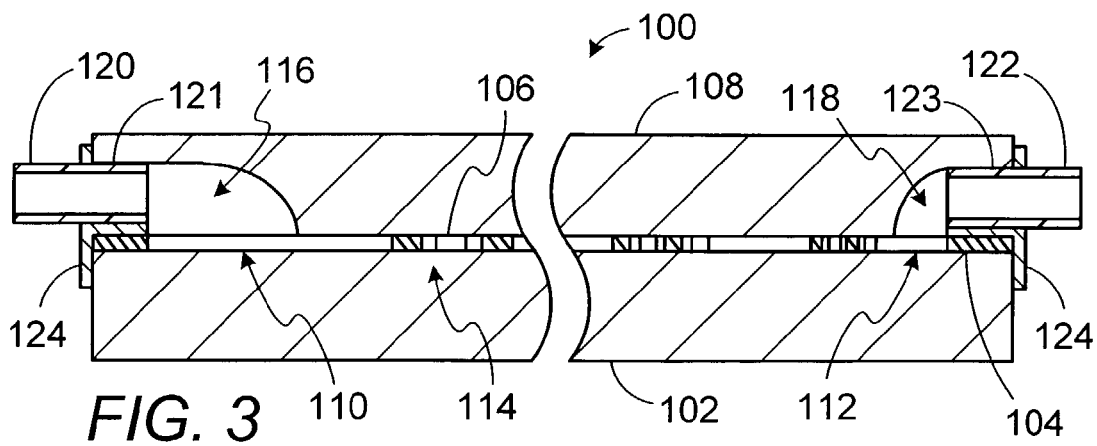
FIG. 3 is a section view taken along line 3—3 in FIG. 1.

A filter in accordance with one embodiment of a present invention, and which is configured to separate particles from a fluid (i.e. a liquid or a gas), is generally represented by reference numeral 100 in FIGS. 1–3. The exemplary filter 100 includes a bottom cover 102, a filter layer 104 with a plurality of filter members 106, and a top cover 108. An inlet region 110, an outlet region 112 and a filter region 114, which contains the filter members 106, are located between the top and bottom covers 102 and 108. The top cover 108 has corresponding inlet and outlet regions 116 and 118. Fluid enters the exemplary filter 100 by way of an inlet tube 120, which is positioned in an inlet slot 121, and exits by way of an outlet tube 122, which is positioned in an outlet slot 123. Sealant material 124 is also provided around the inlet and outlet tubes 120 and 122.

Figure 5:
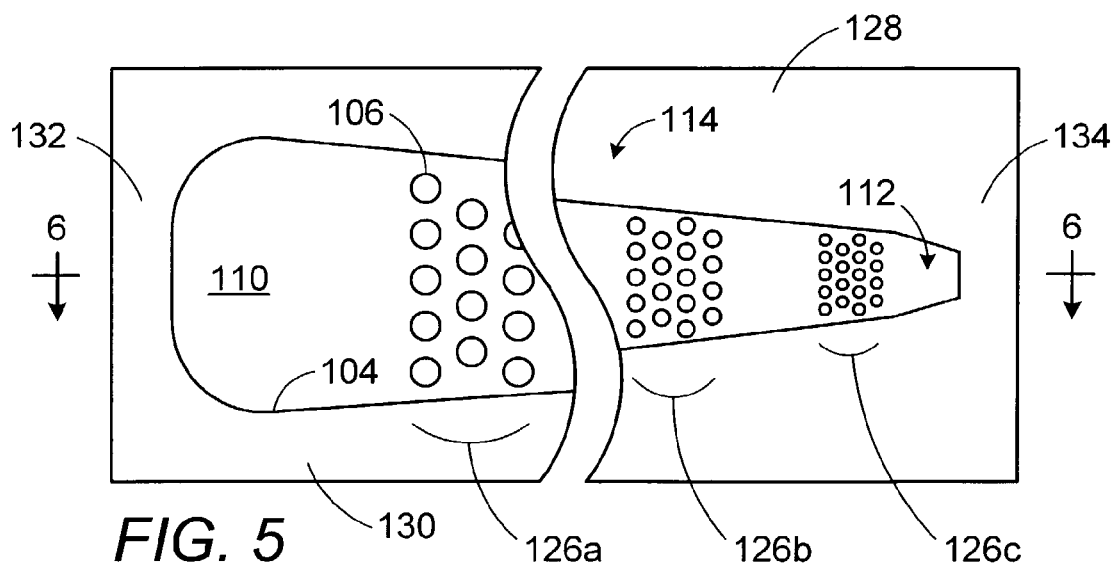
FIG. 5 is a plan view of a cover and a filter layer in accordance with a preferred embodiment of a present invention.

Turning to FIG. 5, the filter members 106 in the exemplary implementation may be arranged in a plurality of filter member groups 126a–c. Each group 126a–c includes a plurality of rows of spaced filter members. The size of the respective filter members 106 in each group may vary. The size of filters members 106 in the groups 126a–c, for example, decreases along the direction of fluid flow (i.e. the largest filter members are closest to the inlet region 110 and the smallest filter members are closest to the outlet region 112). The present inventions are not, however, limited to any particular filter member arrangement. For example, the filter members 106 could be arranged in a single group that occupies all or a portion of the filter region 114. The filter members 106 could also all be the same size or the size could vary randomly within the filter region 114.

The exemplary filter members 106 are generally circular in cross-sectional shape and are perpendicular to the bottom cover 102 and top cover 108. Nevertheless, the filter members 106 are not limited to any particular cross-sectional shape. For example, the cross-sectional shape of the filter members 106 could be elliptical, square, rectangular, hexagonal or any other shape suitable for the intended application. Nor is the orientation of the filter members 106 relative to the bottom cover 102 and top cover 108 limited to the exemplary perpendicular orientation. The filters members 106 need only extend in a direction that is transverse to the direction of fluid flow.

In addition to the filter members 106, portions of the exemplary filter layer 104 also form the walls that define the inlet region 110, outlet region 112 and filter region 114. More specifically, and referring to FIGS. 5 and 6, the filter layer 104 includes a pair of side walls 128 and 130 and a pair of end walls 132 and 134. The walls may, alternatively, be formed in the bottom cover 102 or top cover 108. In either instance, the inner surfaces of the side walls may define a tapered, funnel-like area therebetween (as shown) or be generally parallel to one another.

As illustrated for example in FIGS. 1–3, the inlet and outlet tubes 120 and 122 in the exemplary implementation extend though the end walls of the top cover 108 and are positioned in in-line fashion. Alternatively, the inlet and outlet tubes 120 and 122 could extend through the side walls or the top wall. The inlet tube 120 and/or outlet tube 122 may also be omitted and replaced by other couplings such as, for example, septums configured to receive needles and threaded openings to which syringes and other devices may be coupled. Additionally, the exemplary inlet and outlet tubes 120 and 122 (or other couplings) may be associated with the bottom cover 102, or both the top and bottom covers, instead of the top cover only.

Filters in accordance with the present inventions have a wide variety of applications. Such applications include, but are not limited to, chemical, biological and medical applications. The filters may be used alone to, for example, filter suspended solids from water, separate cells from a liquid medium, select specifically sized pigments and other solids from a liquid medium, or trap specific solids which may then be reclaimed by flushing them from the filter. The filters may also be inserted into a fluid line, such as an intravenous line, or connected to other devices in series or parallel, as discussed below with reference to FIGS. 19A and 19B.

Filters in accordance with the present inventions are also not limited to any particular sizes. In addition to the type of application, the flow rate (determined by the cross-sectional area and length of the filter region) and the size of the particles that will be allowed to pass through the filter (determined by the spacing between the filter members) are also taken into account. The exemplary filter 100, which is well suited for low volume (e.g. about 1 μl to about 1 ml) applications such as drug delivery, is a relatively small device. Here, the bottom cover 102 and top cover 108 would each preferably be about 0.25 mm to about 25 mm in length (measured from the inlet end to the outlet end), about 0.25 mm to about 10 mm wide, and about 0.5 mm to about 2 mm thick. The filter layer 104 would be about 10 μm to about 500 μm thick, while the diameter of the filter members 106 would preferably be about 1 μm to about 100 μm and the spacing therebetween would range from 1 μm to about 100 μm. The inlet and outlet tubes 120 and 122 would have an outer diameter ("OD") between about 0.3 mm and about 0.75 mm and an inner diameter ("ID") between about 0.1 mm and about 0.55 mm.

In one specific implementation, the bottom cover 102 and top cover 108 are each about 25 mm in length, about 5 mm wide, and about 1 mm thick. The filter layer 104 here is about 20 μm thick, while the diameter of the filter members 106 would preferably be about 10 μm with spacing of about 10 μm at the inlet end, while the diameter would be about 1 μm with spacing of about 1 μm at the outlet end. The inlet and outlet tubes 120 and 122 have an OD of about 0.75 mm and an ID of about 0.55 mm.

Figure 4:
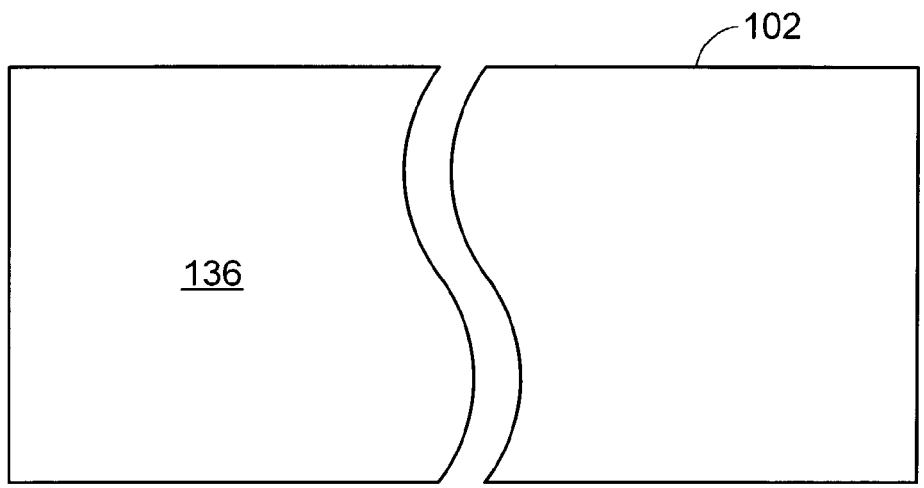
FIG. 4 is a plan view of a cover in accordance with a preferred embodiment of a present invention.
Figure 6:
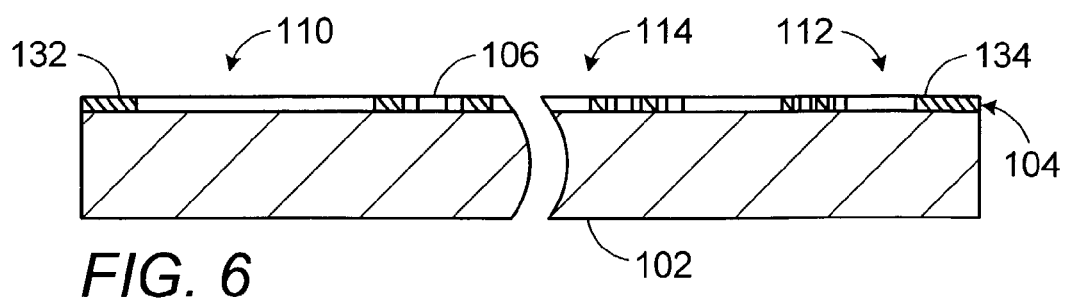
FIG. 6 is a section view taken along line 6—6 in FIG. 5.

Turning to materials and manufacturing, the exemplary bottom cover 102 and top cover 108 may be formed from relatively rigid inert materials such as glass, quartz or silicon. Plastics such as Kapton® and Upilex® may also be used where flexibility is desired. As illustrated in FIG. 4, the bottom cover 102 preferably (although not necessarily) has a generally flat, smooth inner surface 136. The filter layer 104, including the filter members 106 and the walls 128–134, is formed on the bottom cover inner surface 136, as shown in FIGS. 5 and 6. Preferably, the filter layer 104 is formed by a photolithographic process wherein the inner surface 136 is coated with a layer of photoactive material such as, for example, a photoresist (which may be positive or negative photoresist), polyimide or adhesive. An adhesions promoter, such as silane coupling agents, may be added if desired. The layer of photoactive material is then masked and exposed to light. The appropriate portion of the photoactive material layer can then be removed and the remaining photoactive material forms the exemplary filter layer 104. Alternatively, the filter layer 104 may be formed by simply depositing suitable filter layer material, such as Vacrel®, in the appropriate pattern through the use of screen printing or other suitable processes. The bottom cover 102 and filter layer 104 are baked to about 1000° C. after the filter layer 104 has been formed. Alternatively, light curing may be employed.

Figure 7:
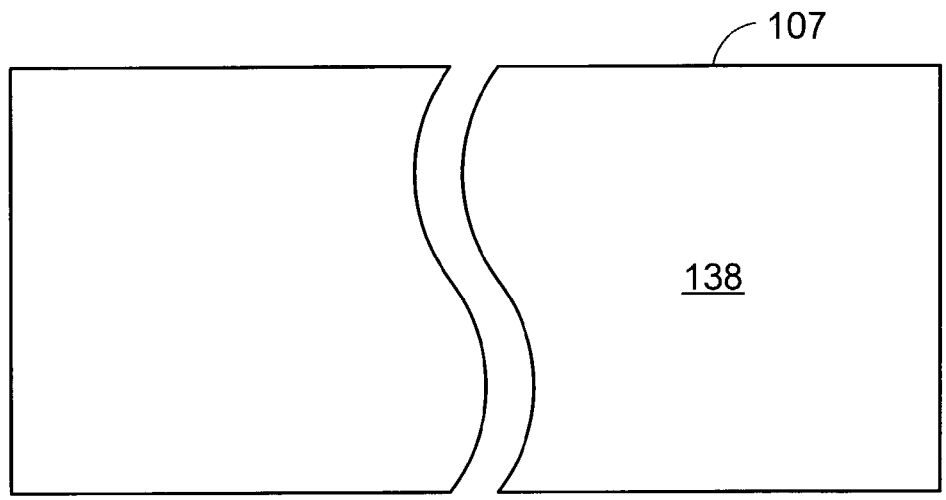
FIG. 7 is a plan view of a cover blank in accordance with a preferred embodiment of a present invention.
Figure 8:
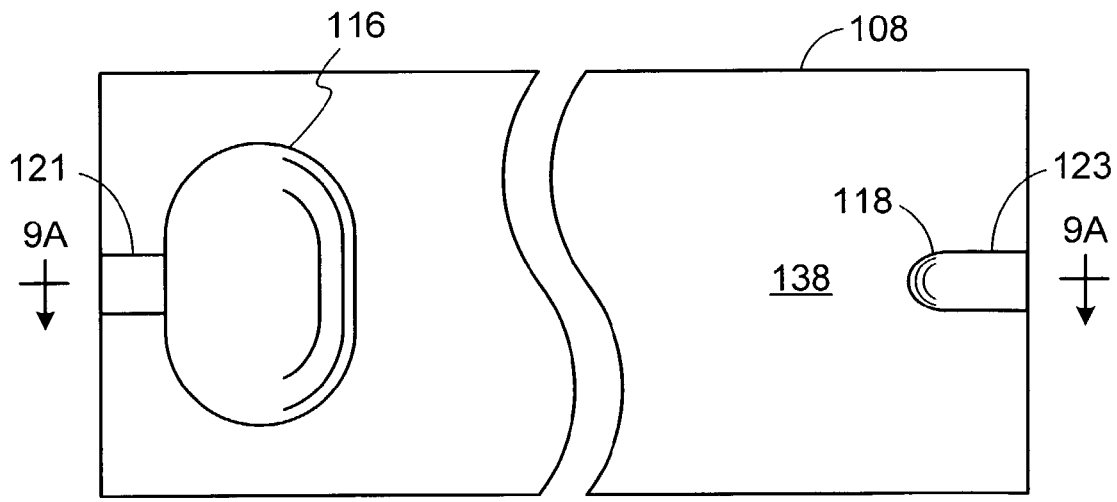
FIG. 8 is a plan view of a cover in accordance with a preferred embodiment of a present invention.
Figure 9A:
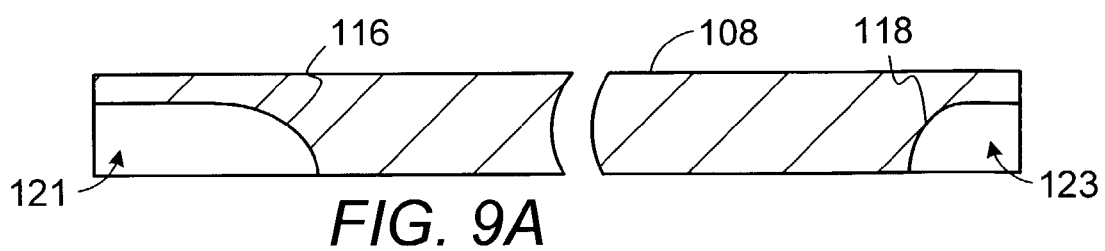
FIG. 9A is a section view taken along line 9A—9A in FIG. 8.
Figure 9B:
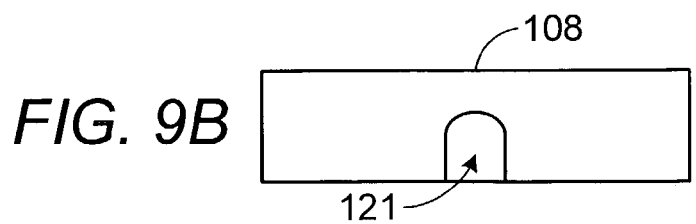
FIG. 9B is an end view of the cover illustrated in FIG. 8.

As illustrated in FIG. 7, manufacture of the exemplary top cover 108 preferably (although not necessarily) initially starts with a glass, quartz or silicon blank 107 that has a generally flat, smooth inner surface 138. The inlet and outlet regions 116 and 118 and inlet and outlet slots 121 and 123 may be formed in the inner surface 138, as is shown in FIGS. 8–9B, through the use of an etching process (either chemical or mechanical) to complete the top cover 108. Alternatively, in those instances where the top cover 108 is formed from plastics or another moldable materials, the top cover may simply be molded with the inlet and outlet regions 116 and 118 and the inlet and outlet slots 121 and 123 in place.

The next step in the exemplary manufacturing process is the mounting of the top cover 108 onto the filter layer 104. More specifically, the top cover 108 is positioned on the filter layer 104 in the manner illustrated in FIG. 3 and is bonded to the filter layer through the use of heat and pressure and/or adhesives. Thus, in addition to filtering particles from fluid, the filter layer 104 also secures the bottom cover 102 to the top cover 108. Once the top cover 108 is in place, the inlet and outlet tubes 120 and 122 may be inserted into the inlet and outlet slots 121 and 123. The sealant material 124 is then applied to create an airtight seal around the inlet and outlet tubes 120 and 122. Suitable sealant materials include encapsulating materials such as UV curable adhesives and other adhesives such as cyanoacrylates. Additionally, in those instances where fluid will be supplied to the exemplary filter 100 under a relatively high pressure, it may be desirable to package the filter. The packaging (not shown) may, for example, take the form of a plastic outer shell or a layer of encapsulating material that extends around the exterior of the bottom cover 102, filter layer 104 and top cover 108.

The materials and photolithographic and screen printing manufacturing processes described above are conventional in the field of semiconductor manufacturing and are relatively inexpensive. Such materials and manufacturing processes also lend themselves to the formation of small structures under tight tolerances.

Figure 10:
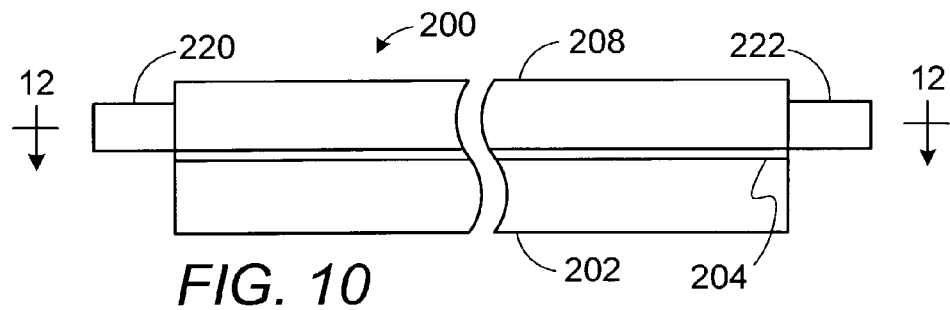
FIG. 10 is a side view of a separation device in accordance with a preferred embodiment of a present invention.
Figure 11:
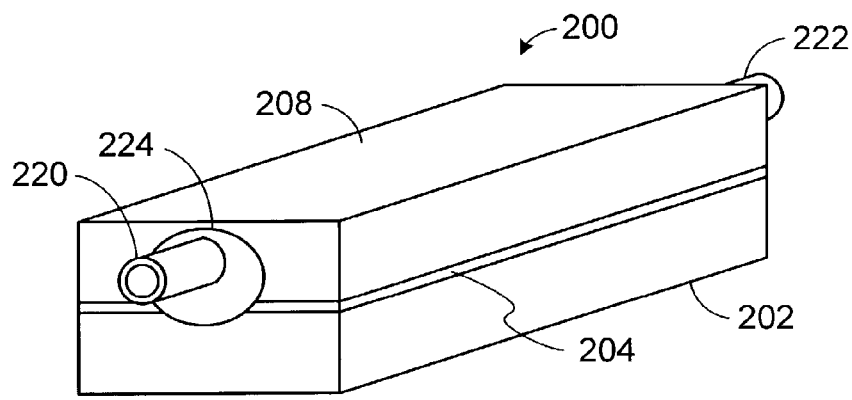
FIG. 11 is a perspective view of the separation device illustrated in FIG. 10.
Figure 12:
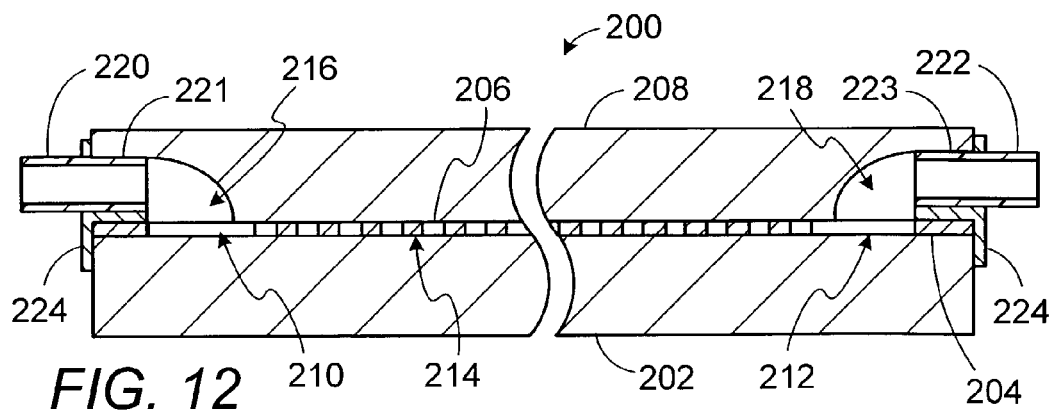
FIG. 12 is a section view taken along line 12—12 in FIG. 10.

A separation line apparatus in accordance with one embodiment of a present invention is generally represented by reference numeral 200 in FIGS. 10–12. Many aspects of the separation line apparatus 200 are similar to those of the filter 100 illustrated in FIGS. 1–3 and similar elements are represented by similar reference numerals. More specifically, the exemplary separation line apparatus 200 includes a bottom cover 202, a separation layer 204 with a separation line 206, and a top cover 208. More specifically, the separation layer 204 has a channel formed therein. The separation layer material on opposite sides of the channel defines the lateral sides of the separation line 206, while the bottom cover 202 and top cover 208 respectively define the bottom and top sides of the separation line. An inlet region 210, an outlet region 212 and a separation region 214 are located between the top and bottom covers 202 and 208. The top cover 208 has corresponding inlet and outlet regions 216 and 218. Fluid enters the exemplary separation line apparatus 200 by way of an inlet tube 220, which is positioned in an inlet slot 221, and exits by way of an outlet tube 222, which is positioned in an outlet slot 223. Sealant material 224 is also provided around the inlet and outlet tubes 220 and 222.

Figure 14:
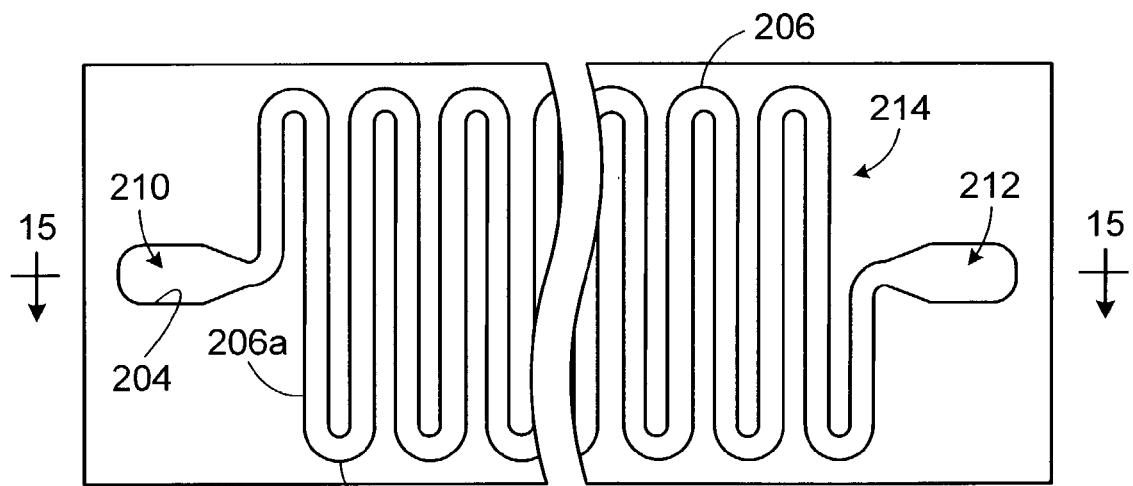
FIG. 14 is a plan view of a cover and a separation layer in accordance with a preferred embodiment of a present invention.

Referring to FIG. 14, the exemplary separation line 206 has a generally serpentine configuration. In other words, the separation line 206 winds back and forth within the separation region 214 in order to maximize the length of the separation line given the available surface area provided by the bottom cover 202. In the exemplary implementation, the separation line 206 includes a plurality of relatively long portions 206a which are connected in series by respective connector portions 206b. The relatively long portions 206a in the exemplary implementation are linear and extend in a direction that is transverse to the longitudinal axis of the separation line apparatus 200, while the connector portions 206b are curved.

It should be noted that "serpentine" separation lines in accordance with the present inventions are not limited to the configuration presented in the exemplary embodiment. For example, the relatively long portions 206a may be curved and, although curved connector portions 206b are preferable, the connector portions do not have to be curved. The separation layer 204 may also be configured such that the relatively long portions 206a extend in the same direction as the longitudinal axis of the separation line apparatus 200. Here, the inlet region 210 could be positioned near one of the side edges of the bottom cover (i.e. one of the long edges) and the outlet region 212 could be positioned near the other. So configured, the separation line 206 would wind back and forth from one longitudinal end of the bottom cover 202 to the other.

As illustrated for example in FIGS. 10–12, the inlet and outlet tubes 220 and 222 in the exemplary implementation extend though the end walls of the top cover 208 and are positioned in in-line fashion. Alternatively, the inlet and outlet tubes 220 and 222 could extend through the side walls or the top wall. The inlet tube 220 and/or outlet tube 222 may also be omitted and replaced by other couplings such as, for example, septums configured to receive needles or threaded openings to which syringes or other devices could be coupled. Additionally, the exemplary inlet and outlet tubes 220 and 222 (or other couplings) may be associated with the bottom cover 202, or both the top and bottom covers, instead of the top cover only.

Separation line apparatus in accordance with the present inventions have a wide variety of applications. Such applications include, but are not limited to, GCMS, FTIR, UV VIS and other forms of spectroscopy. The separation line apparatus may also be used alone or in series with other devices, as described below with reference to FIGS. 19A and 19B.

Separation line apparatus in accordance with the present inventions are also not limited to any particular sizes. In addition to the type of application, the length of the separation line and the flow rate (determined by the cross-sectional area and length of the separation line) are also taken into account. The exemplary separation line apparatus 200, which is well suited for low volume (e.g. about 1 µl to about 1 ml) applications such as forensic chromatography, is relatively small device. Here, the bottom cover 202 and top cover 208 would each preferably be about 0.25 mm to about 25 mm in length (measured from the inlet end to the outlet end), about 0.25 mm to about 10 mm wide, and about 0.5 mm to about 2 mm thick. The separation layer 204 would be about 10 µm to about 1 mm thick, while the width (measured in a direction transverse to fluid flow) of the separation line portions 206a and 206b would preferably be about 1 µm to about 100 µm, with about 1 µm to about 100 µm between adjacent line portions 206a. So configured, the length of the separation line would be about 1 m to about 25 m, assuming that about 2.5 mm on each end of the apparatus is occupied by the inlet and outlet regions 210 and 212 and that the connector portions 206b are about 0.5 mm from the edges of the bottom cover 202. The inlet and outlet tubes 220 and 222 would have an outer diameter ("OD") between about 0.3 mm and about 0.75 mm and an inner diameter ("ID") between about 0.1 mm and about 0.55 mm.

In one specific implementation, the bottom cover 202 and top cover 208 are each about 25 mm in length, about 5 mm wide, and about 1 mm thick. The separation layer 204 here is about 20 µm thick, while the width of the separation line portions 206a and 206b would preferably be about 20 µm, with about 20 µm between adjacent line portions 206a. So configured, the length of the separation line would be about 2 m, with the assumptions described above. The inlet and outlet tubes 220 and 222 have an OD of about 0.75 mm and an ID of about 0.55 mm.

Figure 13:
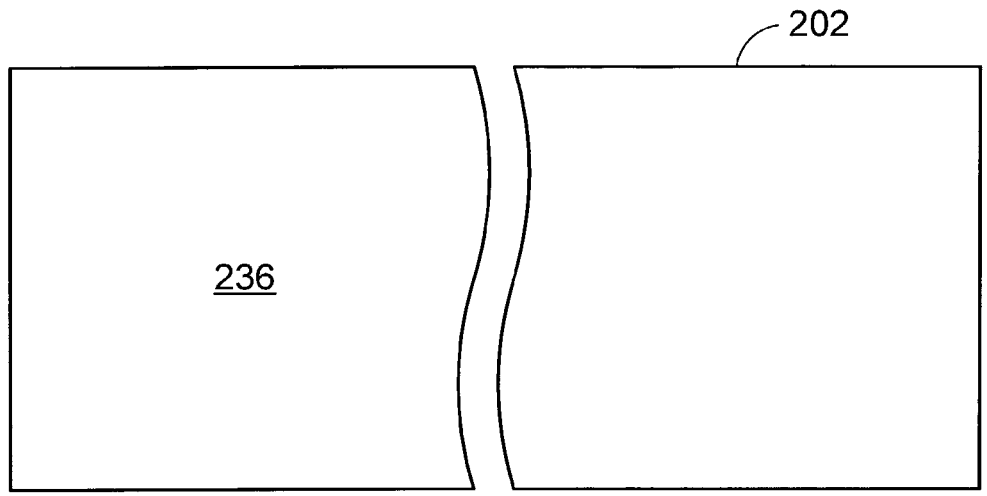
FIG. 13 is a plan view of a cover in accordance with a preferred embodiment of a present invention.
Figure 15:
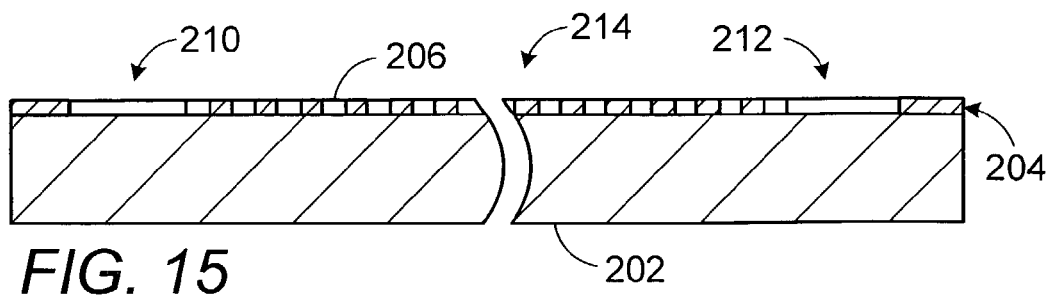
FIG. 15 is a section view taken along line 15—15 in FIG. 14.
Figure 16:
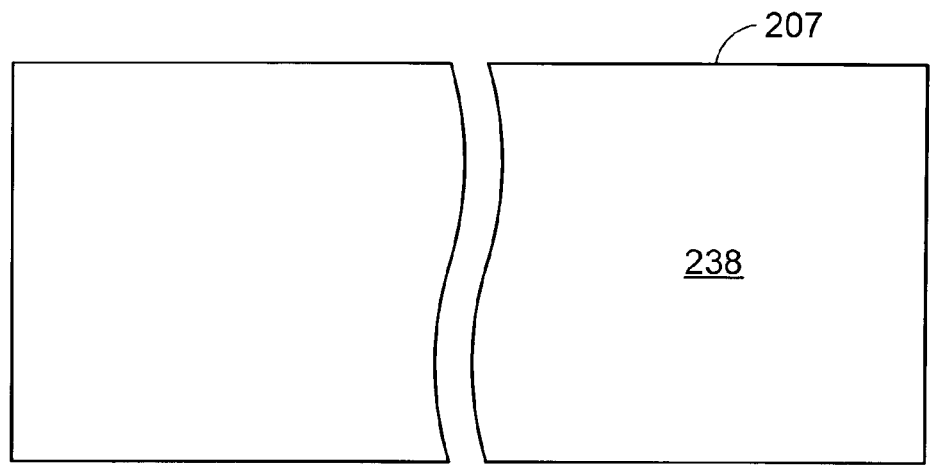
FIG. 16 is a plan view of a cover blank in accordance with a preferred embodiment of a present invention.
Figure 17:
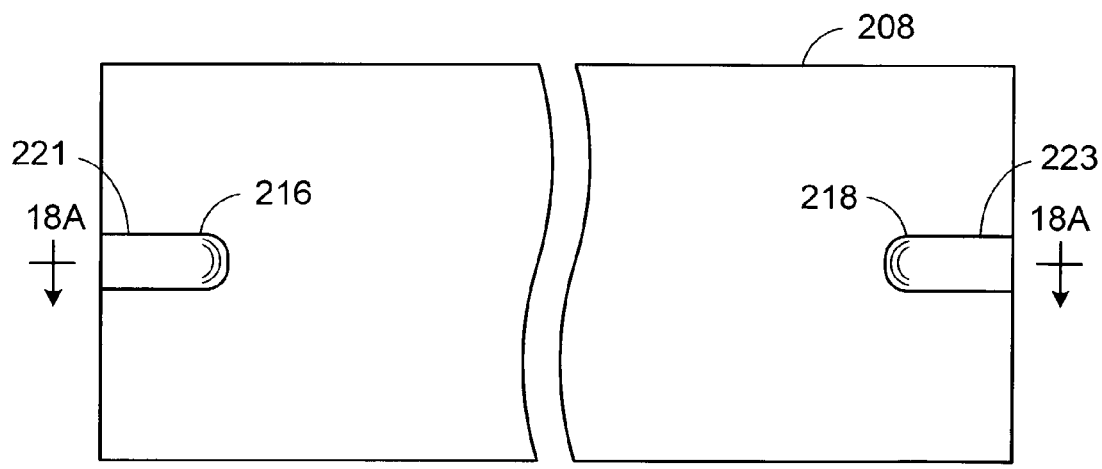
FIG. 17 is a plan view of a cover in accordance with a preferred embodiment of a present invention.
Figure 18A:
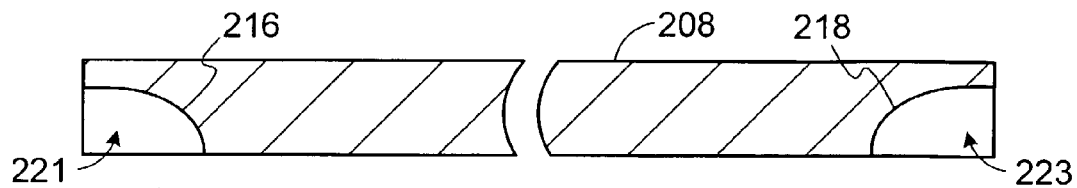
FIG. 18A is a section view taken along line 18A—18A in FIG. 17.
Figure 18B:
FIG. 18B is an end view of the cover illustrated in FIG. 17.

With respect to materials and manufacturing, the exemplary separation line apparatus 200 may be formed with the same materials and processes as the exemplary filter 100. Here too, the exemplary bottom and top covers 202 and 208 may be formed from relatively sturdy inert materials such as glass, silicon and quartz, or plastics such as Kapton® and Upilex®. The bottom cover 202 preferably (although not necessarily) has a generally flat, smooth inner surface 236 as shown in FIG. 13 and the separation layer 204 is formed on the inner surface as shown in FIGS. 14 and 15. Preferably, the separation layer 204 is formed from the materials, and by the photolithographic or printing processes, described above. Turning to FIG. 16, the exemplary top cover 208 preferably (although not necessarily) initially starts with a glass, silicon or quartz blank 207 that has a generally flat, smooth inner surface 238. The inlet and outlet regions 216 and 218 and slots 221 and 223 may be formed through the use of an etching process to complete the top cover 208 illustrated in FIGS. 17–18B. Alternatively, top covers 208 which are formed from plastics or another moldable materials may simply be molded with inlet and outlet regions 216 and 218 and slots 221 and 223 in place.

The top cover 208 may then be mounted onto the separation layer 204 and bonded thereto through the use of heat and pressure and/or adhesives. Thus, in addition to providing a separation line, the separation layer 204 also secures the bottom cover 202 to the top cover 208. Once the top cover 208 is in place, the inlet and outlet tubes 220 and 222 may be inserted into the inlet and outlet slots 221 and 223 and the sealant material 224 applied to create an airtight seal around the inlet and outlet tubes. Additionally, in those instances where fluid will be supplied to the separation apparatus 200 under relatively high pressure, it may be desirable to package the separation apparatus with, for example, plastic outer shell or a layer of encapsulating material.

Figure 19A:
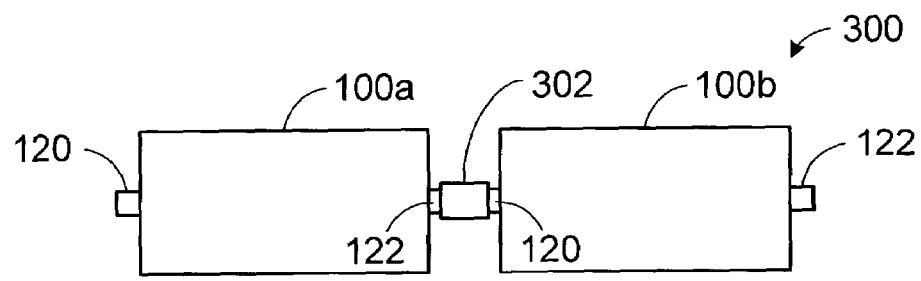
FIG. 19A is a plan view showing two separation devices connected to one another in series.
Figure 19B:
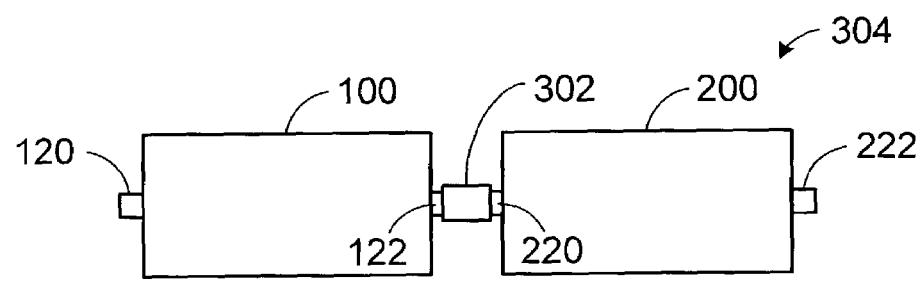
FIG. 19B is a plan view showing two separation devices connected to one another in series.

As noted above, two or more separation devices in accordance with the present inventions may be connected to one another in series or parallel. For example, as illustrated in FIG. 19A, an assembly 300 in accordance with an invention herein includes a pair of filters 100a and 100b that are connected to one another in series. A coupling 302, such as a ring of encapsulating material, may be used to connect the outlet tube 122 of the filter 100a to the inlet tube 120 of the filter 100b. The filters 100a and 100b may, for example, be configured to trap differently sized particles. Turning to FIG. 19B, an assembly 304 in accordance with an invention herein includes a pair of filter 100 and a separation line apparatus 200 that are connected to one another in series by the aforementioned coupling 302. Such an arrangement may be used to remove particles from fluid prior to separation for spectroscopy.

Figure 20:
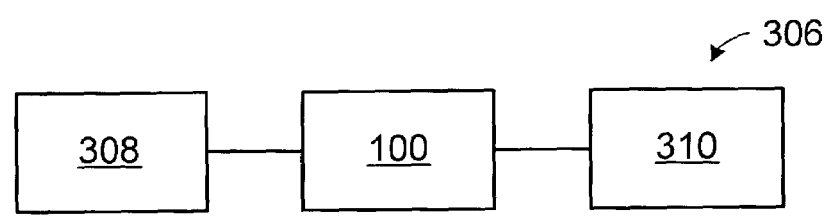
FIG. 20 is a diagrammatic view of a fluid delivery system in accordance with a preferred embodiment of a present invention.
Figure 21:
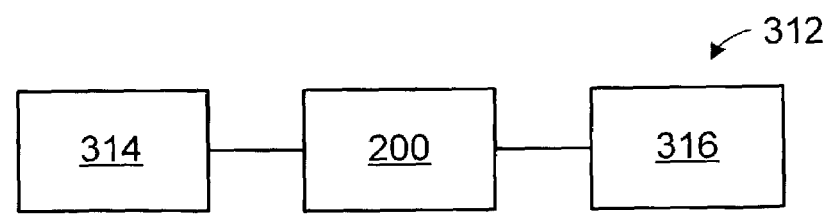
FIG. 21 is a diagrammatic view of a spectroscopy system in accordance with a preferred embodiment of a present invention.

The present inventions also encompass systems that employ the above described filters and separation line apparatus. As illustrated for example in FIG. 20, a fluid delivery system 306 in accordance with a preferred embodiment of a present invention includes a fluid source 308, a filter 100, and a device 310 that receives the filtered fluid. In the medical area, for example, the fluid source 308 may be a source of intravenous fluid and the device 310 may be a needle or other patient interface. Turning to FIG. 21, an exemplary spectroscopy system 312 in accordance with a present invention includes a gas source 314, a separation line apparatus 200, and a spectroscopic analyzer 316 such as a GCMS, FTIR or UV VIS analyzer.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions.

I claim:

1. A filter, comprising:
   first and second covers in spaced relation having a flow region therebetween defining an inlet, an outlet and a flow direction from the inlet to the outlet; and
   a plurality of spaced relatively small filter members of substantially the same size and including a first longitudinal end associated with the first cover and a second longitudinal end associated with the second cover;
   the filter members being located between the inlet and the outlet such that the filter members are in first and second filter member groups that extend transverse to the flow direction, the first filter member group is closer to the inlet than the second filter member group, and the space between respective pairs of adjacent filter members in the first filter member group is greater than the space between adjacent filter members in the second filter member group.

2. A filter, comprising:
   first and second covers in spaced relation having a flow region therebetween defining an inlet, an outlet and a flow direction from the inlet to the outlet;
   a plurality of spaced, relatively small filter members of substantially the same size and formed from different material than the first and second covers located between the inlet and the outlet such that adjacent filter members define a space therebetween and the space between respective pairs of adjacent filter members decreases in the flow direction, each filter member including a first longitudinal end associated with the first cover and a second longitudinal end associated with the second cover; and
   first and second side wall members located on opposite sides of the flow region, each of the side wall members extending from the first cover to the second cover and each of the side wall members being formed from the same material as the filter members;
   the first and second side wall members extending from an area adjacent to the flow region inlet such that inner surfaces of the first and second side walls are generally tapered toward one another in the flow direction.

3. A filter as claimed in claim 1, wherein the filter members are perpendicular to the first and second covers.

4. A filter as claimed in claim 1, wherein the filter members are formed from a different material than the first and second covers.

5. A filter as claimed in claim 1, wherein the filter members are formed from a photoactive material.

6. A filter as claimed in claim 1, wherein the filter members define a height of less than about 500 μm.

7. A filter as claimed in claim 2, wherein the filter members are formed from a photoactive material.

8. A filter as claimed in claim 2, wherein adjacent filter members are less than about 100 μm apart.

9. A filter as claimed in claim 2, wherein the filter members define a width of less than about 100 μm.

10. A filter as claimed in claim 2, wherein the filter members define a height of less than about 500 μm.

11. A filter as claimed in claim 2, wherein the filter members are perpendicular to the first and second covers.

* * * * *